United States Patent [19]
de Meijere et al.

[11] Patent Number: 6,043,393
[45] Date of Patent: Mar. 28, 2000

[54] METHOD FOR PREPARING CYCLOPROPYLAMINES

[75] Inventors: Armin de Meijere, Göttingen, Germany; Vladimir Chaplinski, St. Petersburg; Alexandre Kourdioukov, Tatarstan, both of Russian Federation

[73] Assignee: Bayer Aktiengesellschaft, Leverkusen, Germany

[21] Appl. No.: 09/297,731

[22] PCT Filed: Nov. 5, 1997

[86] PCT No.: PCT/EP97/06100

§ 371 Date: May 6, 1999

§ 102(e) Date: May 6, 1999

[87] PCT Pub. No.: WO98/22425

PCT Pub. Date: May 28, 1998

[30] Foreign Application Priority Data

Nov. 18, 1996 [DE] Germany ............... 196 47 615

[51] Int. Cl.$^7$ .................................. C07C 211/00
[52] U.S. Cl. ............................ 564/322; 564/445
[58] Field of Search ..................... 564/445, 322

[56] References Cited

PUBLICATIONS

Chaplinski, V, et al Angewandte Chemie. Int. Ed Engl 1996 35. No. 4 pp. 413–414

Bolesov, IG et al Journal of Organic Chemistry of the USSR Bd 10 No. 6 Nov. 1974.

*Primary Examiner*—Paul J. Killos
*Attorney, Agent, or Firm*—Joseph C. Gil; Richard E. L. Henderson

[57] ABSTRACT

The present invention relates to a process for preparing cyclopropylamines of the formula

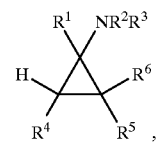

(I)

wherein $R^1$, $R^2$, $R^3$, $R^4$, and $R^5$ have specified meanings, by reacting
(1) a carboxamide of the formula

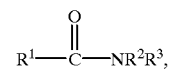

(VI)

wherein $R^1$, $R^2$, and $R^3$ have specified meanings, with
(2) an olefin of the formula

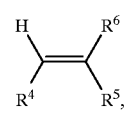

(VII)

wherein $R^4$, $R^5$, and $R^6$ have specified meanings,
(3) alkylmagnesium halides or zinc alkyl compounds of the formula $$R^8\text{—}X \quad (\text{VIII}),$$

wherein $R^8$ has a specified meaning and X represents MgCl, MgBr, MgI, ZnCl, ZnBr, ZnI, or $ZnR^8$, and
(4) orthometallates of the formula (IX)

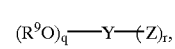

(IX)

wherein $R^9$ has a specified meaning, Y represents Ti, Zr, or V=O, and Z represents chlorine, bromine, or $C_1$–$C_4$-alkyl,
with the provisos that when is Y os Ti or Zr, then is 3 or 4 and r are zero or 1 and the sum q+r=4, and that when Y is V=O, then q represents 3 and r represents zero.

7 Claims, No Drawings

METHOD FOR PREPARING CYCLOPROPYLAMINES

The present invention relates to a process for preparing cyclopropylamines from carboxamides and olefins.

Among the important biologically active cyclopropane derivatives, the cyclopropylamines are most important. A number of aminocyclopropane carboxylic acids occur naturally. Recently, many cyclopropylamines have been used as building blocks of novel medicaments (see Pharnakologie und Toxikologie, Wissenschaftsverlag Mannheim, 1993, p. 655). Cyclopropaneamino acids are of interest, for example, as enzyme inhibitors and for other applications in pharmacology and crop protection. Moreover, it is possible to modify the secondary and tertiary structure of peptide chains in a targeted manner by incorporating cyclopropylamines in key positions. By incorporating cyclopropyl groups, latent instability is created in the centre of the peptide in question, which can react with electrophilic or nucleophilic centres of receptors and enzymes (J. Org. Chem. 54 5866 (1989)). To this end, for example, the cyclopropane-analogue 2,3-methanovalin, which has a fixed confirmation, was prepared instead of the important proteinogenic amino acid valin (ibid.).

For other bioactive amines, too, for example for acetylcholine and 2,5-dimethoxy-4-methylamphetamin, it is possible to synthesize the cyclopropane analogues of fixed confirmation, namely in each case as cis- or trans-diastereomer, to study the receptor geometry and the mechanism of action (J. Med. Chem. 17, 1100 (1974); 18, 1027 (1975); 22, 458 (1979); 25, 526 (1982); 26, 817 (1983) and Chem. Pharm. Bull. 27, 1893 (1979)).

The most important routes which are hitherto known for preparing aminocyclopropane derivatives have been compiled in reviews (The Chemistry of the Cyclopropyl Group, Wiley Interscience 1987, 1342 to 1454). However, only a few of these can be employed generally for preparing differently substituted cyclopropylamines.

There is therefore still a need for a generally applicable, rapid and cost-effective process for preparing a broad range of cyclopropylamines.

This invention, accordingly, provides a process for preparing cyclopropylamines of the formula (I)

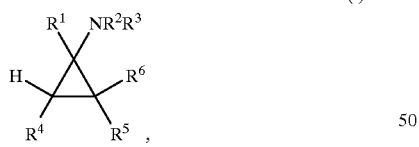

in which
  $R^1$ represents hydrogen, optionally substituted $C_1$–$C_6$-alkyl, optionally substituted $C_2$–$C_6$-alkenyl, optionally substituted $C_3$–$C_7$-cycloalk(en)yl, optionally substituted $C_6$–$C_{10}$-aryl or optionally substituted $C_7$–$C_{12}$-aralkyl and
  $R^2$ and $R^3$ independently of one another each represent optionally substituted $C_1$–$C_6$-alkyl, optionally substituted $C_2$–$C_6$-alkenyl, optionally substituted $C_5$–$C_7$-cycloalk(en)yl, optionally substituted $C_6$–$C_{10}$-aryl or optionally substituted $C_7$–$C_{12}$-aralkyl and
  $R^4$ and $R^5$ either independently of one another and independently of $R^1$ are each defined as $R^1$, where $R^4$ may additionally also represent $N(H)(C_1$–$C_6$-alkyl) or $O$-$C_1$–$C_8$-alkyl, or together represent a bridge of the formulae (II) to (V)

  (II)

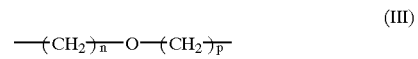  (III)

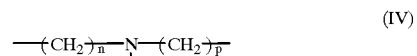  (IV)

(V)

in which
  m represents an integer from 2 to 5 and
  n and p or p' independently of one another each represent zero or an integer from 1 to 4,
  where the sum of n+p is at least 2 and at most 6 and the sum n +p' is at least 1 and at most 4, and
  $R^6$ independently of $R^1$ is as defined for $R^1$, where $R^5$ and $R^6$ together may also represent —$CH_2$—$CH_2$— and
  $R^7$ independently of $R^1$ is as defined for $R^1$, but does not represent hydrogen,
  and where in the formula (IV) independently of one another 1 to 2 $CH_2$ groups may optionally be substituted by $C_1$–$C_4$-alkyl, $C_2$–$C_6$-alkenyl, $C_3$–$C_7$-cycloalk(en)yl, $C_6$–$C_{10}$-aryl or $C_7$–$C_{12}$-aralkyl,
characterized in that a carboxamide of the formula

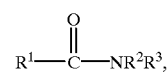  (VI)

in which
  $R^1$, $R^2$ and $R^3$ are each as defined under formula (I), is reacted with an olefin of the formula

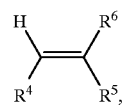  (VII)

in which
  $R^4$, $R^5$ and $R^6$ are each as defined under formula (I) under the action of alkylmagnesium halides or zinc alkyl compounds of the formula $R^8$—X  (VIII), in which
    $R^8$ represents straight-chain or branched $C_1$–$C_6$-alkyl or $C_5$–$C_7$-cycloalkyl and
    X represents MgCl, MgBr, MgI, ZnCl, ZnBr, ZnI or $ZnR^8$,
  and of orthometallates of the formula (IX)

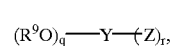  (IX)

in which $R^9$ represents straight-chain or branched $C_1$–$C_6$-alkyl, $C_5$–$C_7$-cycloalkyl or $C_6$–$C_{10}$-aryl, Y represents Ti, Zr or V=O and Z represents chlorine, bromine or $C_1$–$C_4$-alkyl, where in the case Y=Ti or Zr, q represents 3 or 4 and r represents zero or 1 and the sum q+r =4 and, in the case Y=V=O, q represents 3 and r represents zero.

If the radicals $R^1$ to $R^7$ represent alkyl and alkenyl groups, these may be straight-chain or branched, the number of the carbon atoms permitting, and this also applies to the alkyl moiety of aralkyl groups.

If the radicals $R^1$ to $R^7$ represent substituted alkyl, alkenyl, cycloalk(en)yl, aryl and aralkyl groups, suitable substituents are, for example, halogens, $C_1$–$C_4$-haloalkyl, $C_1$–$C_6$-alkoxy, tri-$C_1$–$C_4$-alkyl-silyloxy, di-$C_1$–$C_4$-alkylamino, di-$C_6$–$C_{10}$-arylamino, di-$C_7$–$C_{12}$-arylalkylamino and $C_6$–$C_{10}$—Ar—$C_1$–$C_4$-alkyl. Of these substituents, there may be present, for example, up to 4 identical or different substituents.

$R^1$ preferably represents hydrogen or optionally fluorine- and/or chlorine-substituted $C_1$–$C_4$-alkyl.

$R^2$ and $R^3$ are preferably identical and preferably represent unsubstituted $C_1$–$C_4$-alkyl, $C_1$–$C_4$-alkoxy, phenyl or benzyl.

$R^4$ preferably represents hydrogen, optionally fluorine- and/or chlorine-substituted $C_1$–$C_4$-alkyl, optionally fluorine- and/or chlorine-substituted $C_2$–$C_4$-alkenyl or optionally fluorine-, trifluoromethyl- and/or chlorine-substituted phenyl.

$R^5$ preferably represents hydrogen, optionally fluorine- and/or chlorine-substituted $C_1$–$C_4$-alkyl or phenyl.

Preference is also given to $R^4$ and $R^5$ together representing a bridge of the formulae (II) to (V) where m preferably represents 3 or 4, n and p or p' independently of one another each represent 1 or 2 and $R^7$ preferably represents unsubstituted $C_1$–$C_4$-alkyl, phenyl or benzyl.

$R^6$ preferably represents hydrogen or together with $R^5$ represents —$CH_2$—$CH_2$—.

$R^8$ and $R^9$ independently of one another each preferably represent ethyl, i-propyl, n-butyl or $C_5$–$C_7$-cycloalkyl.

X preferably represents MgBr or $ZnR^8$.

In the process according to the invention, particular preference is given to using dimethyl- or dibenzylformamide as carboxamide; 1,3-butadiene, styrene or N-benzyl-3-pyrroline as olefin; n- or i-propyl- or n-butyl-magnesium bromide or cyclopentyl- or cyclohexylmagnesium chloride or bromide as compound of the formula (VIII) and tetraethyloxy- or tetraisopropyloxytitanium as orthometallate.

The process according to the invention can be carried out, for example, by initially charging a solution of an orthometallate of the formula (IX), adding a solution of an olefin of the formula (VII) and a carboxamide of the formula (VI), followed by addition of a solution of a compound of the formula (VIII).

It is also possible to proceed by adding a solution of a compound of the formula (VIII) to a solution containing a carboxamide of the formula (VI), an orthometallate of the formula (IX) and an olefin of the formula (VII).

Apart from these embodiments, other embodiments are also possible.

Suitable solvents are, for example, ethers, such as dialkyl ethers and tetrahydrofuran. Preference is given to using tetrahydrofuran and mixtures of tetrahydrofuran and diethyl ether which contain at least 70% by weight of tetrahydrofura. The solvent is expediently water-free.

From 0.7 to 5 mols, for example, of an olefin of the formula (VII) can be employed per mole of a carboxamide of the formula (VI). This amount is preferably from 0.9 to 2.5 mol.

From 0.9 to 1.5 equivalents, for example, of an orthometallate of the formula (IX) can be employed per equivalent of a carboxamide of the formula (VI). This amount is preferably from 1 to 1.3 equivalents.

a) At least 2.4 mols, for example, of a compound of the formula (VIII) where x represents a halogen-containing radical, or b) at least 1.2 mols of a compound of the formula (VIII) where X represents $ZnR^8$ can be employed per mole of a carboxamide of the formula (VI). In case a), preference is given to from 2.5 to 3.5 mols, in case b), preference is given to from 1.5 to 2 mols of the compound of the formula (VIII) per mole of carboxamide of the formula (VI). If, in the formula (VIII), $R^8$ represents methyl and/or, in the formula (VIII), X represents $ZnR^8$ where $R^8$ =methyl, it is generally advantageous, in case a), to employ at least 3 moles of such a compound of the formula (VIII) or, in case b), to employ at least 2 moles of such a compound of the formula (VIII).

The compound of the formula (VIII) can be added, for example, at from –40 to +67° C. This temperature is preferably from –30 to +30° C. After the addition of the compound of the formula (VIII) has ended, it is advantageous to continue stirring for some time, for example at from +10 to +70° C. for from 30 minutes to 5 hours. The total reaction time (from the beginning of the addition of the compound of the formula (VIII)) can, for example, be from 1 to 24 hours.

The reaction mixture reacted to exhaustion can be worked up in various ways. It is possible, for example, to distill off the reaction products from the mixture. It is also possible to admix the reaction mixture reacted to exhaustion with Aater and to acidify it slightly, to filter off and wash the precipitate which is then present, to extract the combined organic phases, to draw off the solvent from the extract and to purify the residue, if required, further. It is also possible to make the mixture alkaline after the hydrolysis and to separate off the reaction products by steam distillation. Other work-up methods are also possible.

The process according to the invention is highly regioselective and generally affords only one diastereomer of the cyclopropylamine of the formula (I). If a cyclic olefin of the formula (VII) is employed (where $R^4$ and $R^5$ =together a bridge of the formulae (II) to (V)) or where $R^5$ aid $R^6$ =together —$CH_2$—$CH_2$—, generally only exo products of the formula (I) are formed. In the rare cases where mixtures of diastereomers are obtained, these can be separated in a simple manner, for example by column chromatography, if required.

The process according to the invention is generally applicable and gives, as can be seen from the examples below, excellent results.

EXAMPLES

Example 1

Preparation of exo-3-benzyl-6-N,N-benzylamino-3-azabicyclo[3.1.01]-hexane (formula (I) where $R^1$=hydrogen, $R^2$ =$R^3$ =benzyl, $R^4$ and $R^5$ together represent a bridge of the formula (IV) where $R^6$ =benzyl).

At room temperature and under an atmosphere of nitrogen, a solution of 10.00 g of N-benzyl-3-pyrroline (Synth. Commun. 20, 227 (1990)) and 15.29 g of N,N-dibenzylformamide (Houben-Weyl, Methoden der organischen Chemie, Volume E/5 Part 2, Thieme-Verlag, Stuttgart, 1985, p. 972) in 200 ml of dry tetrahydrofuran was added to a solution of 19.29 g of tetraisopropyloxytitanium in 200 ml of anhydrous tetrahydrofuran. The resulting solution was cooled to −30° C., and 273.8 ml of a 0.62 molar solution of isopropylmagnesium bromide in tetrahydrofaran was added at this temperature with vigorous stirring over a period of 10 minutes, using a steel syringe needle. The mixture was vigorously stirred at from −30 to −10° C. for another 2 hours and then heated at reflux for 3 hours. During this, the colour of the mixture changed to black-brown, and a precipitate precipitated out. The reaction mixture was cooled to room temperature and then slowly admixed with 150 ml of saturated aqueous armmonium chloride solution and 100 ml of water and stirred vigorously until the black titanium complexes had decomposed (1 hour). The white precipitate which was then present was filtered off, the filter cake was washed with 100 ml of diethyl ether and the product was extracted from the filtrate twice using 200 ml of diethyl ether in each case. The combined organic extracts were dried over magnesium sulphate and the solvent was drawn off on a rotary evaporator. To precipitate out polar impurities, 200 ml of petroleum ether were added, the solution was filtered off from the precipitate and the solvent was evaporated off from the filtrate, which was subsequently subjected to fractional distillation. This gave two fractions, namely, at from 60 to 90° C. and 0.07 mbar, 4.59 g of unreacted N-benzyl-3-pyrroline and, at from 90 to 105° C. and 0.07 mbar, by-products (mainly (E)- and (Z)- N,N-dibenzyl-(2-methylcyclopropyl)-amine).

The distillation residue was admixed with 50 ml of petroleum ether and the mixture was filtered through silica gel. After removal of the petroleum ether from the filtrate, 9.16 g (=39.6% of theory) of the product remained in the form of a yellowish viscous oil. Based on reacted N-benzyl-3-pyrroline, the yield was 73.2% of theory.

TLC control [pentane/diethyl ether (2:1)] showed a spot with $R_f$=0.78.

$^1$H NMR (250 MHz, CDCl$_3$): δ=1.27 (s, 2H, H-1, H-5); 2.21 (s, 1H, H-6); 2.31 $^{2j}$HH 8.66 Hz, 2H, H-2, H-4); 2.88 (d, $^{2j}$HH 8.66 Hz, 2H, H'-2, H'4); 3.56 (s, 2H, =NC$\underline{H}_2$Ph); 3.65 (s, 4H, N(C$\underline{H}_2$Ph)$_2$); 7.26–7.33 (m, 15H, Ph).

$^{13}$C NMR (62.9 MHz, CDCl$_3$): δ=25.64 (−, C-1, C-5); 44.95 (−, C-6); 54.41 (+C4); 58.82 (+, N(C$\underline{H}_2$Ph)$_2$); 59.12 (+, =NC$\underline{H}_2$Ph); 126.67 (−, C-Ph); 126.75 (−, C-Ph); 127.92 (−, C-Ph); 128.06 (−, C-Ph); 128.43 (−, C-Ph); 129.44 (−, C-Ph); 138.91 (quart, 2C, NBn$_2$); 139.52 (quart, =NBn).

Example 2

Preparation of (E)- and (Z)-N,N-dibenzyl-(2-phenylcyclopropyl)-amine (formula (I) where $R^1$=hydrogen, $R^2$=$R^3$=benzyl, $R^4$=phenyl, $R^5$=hydrogen).

At room temperature and under an atmosphere of nitrogen, 5.95 ml of a 2.1 molar solution of n-butylmagnesium bromide in diethyl ether were added over a period of 1 hour to a solution of 1.13 g of N,N-dibenzylformamide, 1.14 g of tetraethyloxytitanium and 0.78 g of styrene in 50 ml of anhydrous tetrahydrofuran. The black reaction mixture was stirred for another hour at room temperature and then admixed with 30 ml of a saturated aqueous ammonium chloride solution and 15 ml of water, during which the internal temperature was kept at from 10 to 20° C., and stirring was continued until discolorization. The organic phase was then separated off, the aqueous phase was extracted with 10 ml of diethyl ether, the combined organic phases were dried over magnesium sulphate and the solvent was drawn off under reduced pressure.

Column chromatography of the residue over 20 g of silica gel [pentane/diethyl ether (50:1)] gave fraction I: 366 mg (23.4%) of (Z)-N,N-dibenzyl-(2-phenylcyclopropyl)-amine ($R_f$=0.63), $^1$H NMR (250 MHz, CDCl$_3$): 6=0.75 (m, 1H, 2-H); 0.88 (m, 1H, 2-H); 1.96 (m, 1H); 2.05 (m, 1H); 3.20 (d, $^2$H =14.2 Hz, 2H, CHHPh); 3.48 (d, $^2$H =14.2 Hz, CHHPh); 6.90–7.40 (m, 15H, Ph-H).

$^{13}$C NMR (62.9 MHz, CDCl$_3$, additionally DEPT): δ=13.60 (−, C-3); 23.84 (+, C-2); 43.76 (+, C-1); 57.43 (−, CH$_2$Ph); 125.52 (+, Ph-C); 126.76 (+, Ph-C); 127.55 (+, Ph-C); 128.22 (+, Ph-C); 128.59 (+, Ph-C); 129.56 (+, Ph-C); 138.28 (C$_{quart}$, Ph-C); 138.41 (C$_{quart}$, Ph-C).

Fraction II: 815 mg (52.0%) of (E)-N,N-dibenzyl-(2-phenylcyclopropyl)-amine [N,N-dibenzyltranylcypromine] ($R_f$=0.26), colourless oil.

$^1$H NMR (250 MHz, CDCl$_3$): δ=0.95 (m, 1H, 2-H); 1.04 (m, 1H, 2-H); 1.80 (m, 1H); 2.00 (m, 1H); 3.63 (d, $^2$J=13.0 Hz, 2H, C$\underline{H}$HPh); 3.48 (d, $^2$J=13.0 Hz, 2H CH$\underline{H}$Ph); 6.74–6.82 (m, 2H, Ph-H); 7.03–7.35 (m, 13H, Ph-H).

$^{13}$C NMR (62.9 MHz, CDCl$_3$, additionally DEPT): δ=17.61 (−, C-3); 26.47 (+, C-2); 47.65 (+, C-1); 58.50 (−, CH$_2$Ph); 125.38 (+, Ph-C); 125.78 (+, PhC); 126.90 (+, Ph-C); 128.01 (+, Ph-C); 128.11 (+, Ph-C); 129.40 (+, Ph-C); 138.70 (C$_{quart}$, Ph-C); 142.06 (C$_{quart}$, Ph-C).

HRMS C$_{23}$H$_{23}$N: Calc. 313.1830 (correct HRMS).

Example 3

Preparation of (E)-N,N-dimethyl-(2-ethenylcyclopropyl)-amine (formula (I) where $R^1$=hydrogen, $R^2$=$R^3$=methyl, $R^4$=ethenyl, $R^5$=hydrogen).

Under an atmosphere of nitrogen and at an internal temperature of −20 to −10° C., 267 ml of a 2.25 molar solution of n-butylmagnesium chloride in diethyl ether were added with vigorous stirring over a period of 2 hours to a solution of 14.6 g of N,N-dimethylformamide, 56.9 g of tetraisopropyloxytitanium and 21.6 g of 1,3-butadiene in 600 ml of anhydrous tetrahydrofuran, which was kept at an internal temperature of −20° C. The black reaction mixture was stirred at this temperature for another hour and subsequently at room temperature for a further hour, then cooled to 0° C. and decomposed at an internal temperature of from 5 to 10° C. by careful addition of 600 ml of 20% strength by weight aqueous sulphuric acid. After all solid products had dissolved, the acidic aqueous phase was separated off and, to remove non-basic volatile organic substances (essentially tetrahydrofuran and isopropanol), concentrated at 50° C. on a rotary evaporator at a pressure of 26 mbar for 30 minutes. The solution that remained was cooled to 0° C. and adjusted, with cooling, to a pH of 12 using 40% strength by weight of aqueous sodium hydroxide solution. The product (upper layer) was extracted twice with 100 ml of pentane each time, the combined organic extracts were dried over potassium carbonate and the solvent was distilled off via a 30 cm Vigreaux column. Distillation of the residue at 350 mbar gave 9.76 g=43.9% of theory of the product with a boiling point of 73° C. in the form of a colourless oil.

$^1$H NMR (250 MHz, CDCl$_3$): δ=0.63 (m, 1H, 2-H); 0.85 (m, 1H; 2-H); 1.43 (m, 1H); 1.52 (m, 1H); 2.29 (s, 6H, CH$_3$); 4.85 (dd, $^2$J=1.5, $^3$J$_{ci}$=9.7 Hz, 1H, ethenyl-H$_B$); 5.00 (dd, $^2$J=1,5, $^3$J$_{trans}$=16.4 Hz, 1H, ethenyl-H$_A$); 5.42 (m, 1H, ethenyl-H$_x$).

$^{13}$C NMR (62.9 MHz, CDCl$_3$, additionally DEPT): δ=15.54 (−, C-3); 24.31 (+, C-2); 44.97 (+, CH$_3$); 48.47 (+, C-1); 112.22 (−, C-2'); 139.75 (+, C-1').

The product was contaminated with 6% by weight of (E)-N,N-dimethyl-(2- ethylcyclopropyl)-amine. The product can be purified further as the hydrochloride by recrystallization from boiling dioxane (50 ml to 1 g).

Examples 4 to 8

Preparation of 3-benzyl-exo-6-(N,N-dibenzylamino-3-azabicyclo[3.1.0]-hexane

Example 4

At room temperature and under nitrogen, methyltriisopropoxytitanium (15.1 g), over a period of 5 min, and then a solution of cyclohexylmagnesium bromide in diethyl ether (45.23 ml, 2.1 M), over a period of 10 minutes, were added to a stirred solution of N-benzyl-3-pyrroline (10.0 g) and N,N-dibenzylformamide (14.14 g) in anhydrous tetrahydrofuran (100 ml). The mixture was stirred vigorously at 60–70° C. for 37 hours. After cooling to room temperature, 50 ml of $H_2O$ were added to the reaction mixture, and the white precipitate was filtered off and washed with diethyl ether (50 ml). The filtrate was dried over $MgSO_4$ and the solution was concentrated under reduced pressure. The unreacted N-benzyl-3-pyrroline (1.2 g) was distilled off under reduced pressure (0.07 mbar, boiling range 55–60° C.), oil bath temperature 120–140° C.). The residue was crude 3-benzyl-exo-6-(N,N-dibenzylamino)-3-azabicyclo [3.1.0]hexane, contaminated with, for example, dibenzylforrnarnide. Purification by filtration through a layer of silica gel (10 g, mobile phase ether/hexane 1:6) and evaporation of the resulting solution gave the product (19.4 g, 84%) as a slightly yellowish viscous oil).

Example 5

At room temperature, a solution of methylmagnesium chloride (3.4 ml, 3 M in tetrahydrofuran) was added dropwise over a period of 10 min to a mixture of N-benzyl-3-pyrroline (1.48 g) and tetraisopropoxytitanium (2.72 ml, 9.3 mmol) tetrahydrofuran. After the solution had stirred for a further 10 min, a solution of dibenzylformamide (2.1 g) in 5 ml of tetrahydrofuran was added at room temperature over a period of 30 seconds. A solution of cyclohexylmagnesium bromide (5.2 ml, 1.95 M in diethyl ether) was then added dropwise over a period of 2 hours, and the mixture was heated under reflux for another 4 hours. The hot reaction mixture was admixed with water (5 ml) (careful, exothermic reaction), and the resulting precipitate was collected on a filter and washed with 20 ml of diethyl ether. The combined filtrates were concentrated under reduced pressure. Unreacted N-benzyl-3-pyrroline. Dibenzylformamide and unidentified compounds were distilled off from the residue under reduced pressure $1.3 \times 10^{-4}$ mbar, bath temperature 150° C.). Further distillation (bath temperature 180–200° C.) gave 3-benzyl-6-(dibenzylamino)-3-azabicyclo[3.1.0] hexane (2.62 g, 90% pure according to $^1H$ NMR, corresponding to a yield of 69%), contaminated by dibenzylformamide, as a slightly yellowish viscous oil.

Example 6

At room temperature, a solution of methylmagnesium chloride (3.4 ml, 3 M in tetrahydrofuran) was added dropwise over a period of 10 minutes to a solution of N-benzyl-3-pyrroline (1.48 g) and chloroisopropoxytitanium (2.42 g) in 4 ml of anhydrous tetrahydrofuran. After the mixture had stirred for a further 10 minutes, a solution of dibenzylformamide (2.1 g) in 6 ml of tetrahydrofuran was added at room temperature over a period of 30 seconds. Over a period of 2 hours, a solution of cyclohexylmagnesium bromide (5.2 ml, 1.95 M in diethyl ether) was then added dropwise over a period of 2 hours, and the mixture was heated under reflux for another 4 hours. 5 ml of water (careful, exothermic reaction) were added the hot reaction mixture, and the precipitated precipitate was filtered off and washed with 20 ml of diethyl ether. The combined filtrates were concentrated under reduced pressure, and the residue was distilled under reduced pressure $1.3 \times 10^{-4}$ mbar, oil bath temperature of 120–150° C.) to remove unreacted N-benzyl-3-pyrroline, dibenzylformamide and other, unidentified impurities. Distillation of the main product at a bath temperature of 180–200° C. gave 3-benzyl-6-(dibenzylamino)-3-azobicyclo[3.1.0]hexane (2.52 g, 91% purity according to $^1H$ NMR, corresponding to a yield of 67%), contaminated by dibenzylformamide, as a slightly yellowish viscous oil).

Example 7

At 25–40° C. and under an atmosphere of nitrogen, titanium tetrachloride (0.77 ml) was added with stirring (careful, exothermic reaction) over a period of 5 minutes to titanium tetraisopropoxide (6.23 ml), and the mixture was briefly (for 5 minutes) heated with stirring to 80° C. The chlorotriisopropoxytitanium, which was formed quantitatively, was cooled to room temperature, and at room temperature, a solution of N-benzyl-3-pyrroline (5.2 g) and dibenzylformamide (7.3 g) in anhydrous tetrahydrofuran (80 ml) was added to it over a period of 5 minutes, and a solution of cyclohexylmagnesium bromide in ether (39.2 ml, 2.1 M) was then added at 30–40° C. over a period of 30 minutes (exothermic reaction). The mixture was stirred at 40–45° C. for 31 hours. 20 ml of water were added to the reaction mixture (exothermic reaction), and the white precipitate was collected on a filter and washed with 40 ml of diethyl ether. The combined filtrates were dried over magnesium sulphate, the solution was concentrated under reduced pressure and the unreacted N-benzyl-3-pyrroline (1.35 g) was removed under reduced pressure (0.07 mbar), boiling range 55–60° C., oil bath temperature 120–140° C.). The residue was crude 3-benzyl-exo-6-(N,N-dibenzylamino) -3-azabicyclo [3.1.0]hexane, contaminated by some dibenzylformamide. Purification was carried out by filtration through a layer of silica gel (8.0 g, mobile phase hexane), concentration of the resulting solution under reduced pressure, yield 8.35 g (70%) as a yellowish viscous oil.

Example 8

At room temperature and under nitrogen, a solution of N-benzyl-3-pyrroline (87.8 g) and dibenzylformamide (12.4 g) in anhydrous tetrahydrofuran (90 ml) was admixed with stirring with methyltriisopropoxytitanium (13 ml) over a period of 5 minutes and then, at 30–40° C., with a solution of cyclohexylmagnesium bromide in diethyl ether (41.5 ml, 2.0 M) (careful, exothermic reaction) over a period of 30 minutes. At 65–75° C., the mixture was stirred vigorously for 41 hours. 25 ml of water were added to the reaction mixture (exothermic reaction) the precipitated white precipitate was filtered off, washed with 30 ml of diethyl ether and the combined filtrates were dried over $MgSO_4$. The solution was concentrated under reduced pressure, and the unreacted N-benzyl-3-pyrroline (2.6 g) was distilled off under reduced pressure (0.07 mbar, boiling range 55–60° C.), oil bath temperature 120–140° C). The residue was crude 3-benzyl-exo-6-(N,N-dibenzylamino)-3-azabicyclo [3.1.0]-hexane, contaminated with some dibenzylformamide. The mixture was filtered through a layer of silica gel (10 g, mobile phase/hexane) the resulting solution was concentrated under reduced pressure and the title compound (13.4 g, 66%) was obtained as a slightly yellowish viscous oil).

What is claimed is:

1. A process for preparing cyclopropylamines of the formula

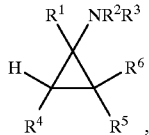  (I)

wherein

R$^1$ represents hydrogen, optionally substituted C$_1$–C$_6$-alkyl, optionally substituted C$_2$–C$_6$-alkenyl, optionally substituted C$_3$–C$_7$-cycloalk(en)yl, optionally substituted C$_6$–C$_{10}$-aryl, or optionally substituted C$_7$–C$_{12}$-aralkyl, R$^2$ and R$^3$ independently of one another each represent optionally substituted C$_1$–C$_6$-alkyl, optionally substituted C$_2$–C$_6$-alkenyl, optionally substituted C$_5$–C$_7$-cycloalk(en)yl, optionally substituted C$_6$–C$_{10}$-aryl, or optionally substituted C$_7$–C$_{12}$-aralkyl, R$^4$ and R$^5$ either independently of one another and independently of R$^1$ are each defined as R$^1$, where R$^4$ may additionally also represent N(H)(C$_1$–C$_6$-akyl) or O—C$_1$–C$_8$-alkyl, or R$^4$ and R$^5$ together represent a bridge of one of the formulae (II) to (V)

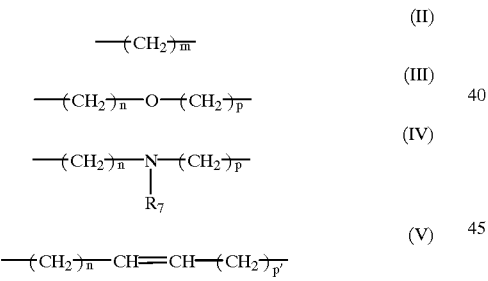

wherein m represents an integer from 2 to 5 and n and p or p' independently of one another each represent zero or an integer from 1 to 4, where the sum of n+p is at least 2 and at most 6 and the sum n+p' is at least 1 and at most 4, R$^6$ independently of R$^1$ is as defined for R$^1$, where R$^5$ and R$^6$ together may also represent —CH$_2$—CH$_2$—, and R$^7$ represents optionally substituted C$_1$–C$_6$-alkyl, optionally substituted C$_2$–C$_6$-alkenyl, optionally substituted C$_3$–C$_7$-cycloalk(en)yl, optionally substituted C$_6$–C$_{10}$-aryl, or optionally substituted C$_7$–C$_{12}$-aralkyl, and where in the formula (IV) independently of one another 1 to 2 CH$_2$ groups may optionally be substituted by C$_1$–C$_4$-alkyl, C$_2$–C$_6$-alkenyl, C$_3$–C$_7$-cycloalk(en)yl, C$_6$–C$_{10}$-aryl, or C$_7$–C$_{12}$-aralkyl, comprising reacting (1) a carboxamide of the formula

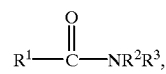  (VI)

wherein R$^1$, R$^2$, and R$^3$ are each as defined for formula (I), with (2) an olefin of the formula

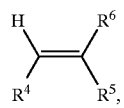  (VII)

wherein R$^4$, R$^5$, and R$^6$ are each as defined for formula (I), (3) alkylmagnesium halides or zinc alkyl compounds of the formula

  (VIII), wherein

R$^8$ represents straight-chain or branched C$_1$–C$_6$-alkyl or C$_5$–C$_7$-cycloalkyl, and X represents MgCl, MgBr, MgI, ZnCl, ZnBr, ZnI, or ZnR$^8$, and (4) orthometallates of the formula (IX)

  (IX)

wherein

R$^9$ represents straight-chain or branched C$_1$–C$_6$-alkyl, or C$_5$–C$_7$-cycloalkyl, or C$_6$–C$_{10}$-aryl, Y represents Ti, Zr, or V=O, and Z represents chlorine, bromine, or C$_1$–C$_4$-alkyl, with the provisos that when Y is Ti or Zr, then q represents 3 or 4 and r represents zero or 1 and the sum q+r=4, and that when Y is V=O, then q represents 3 and r represents zero.

2. A process according to claim 1 wherein the radicals R$^1$ to R$^7$, if they represent substituted alkyl, alkenyl, cycloalk(en)yl, aryl, or aralkyl groups, independently of one another contain up to four identical or different substituents selected from the group consisting of the halogens, C$_1$–C$_6$-alkoxy groups, tri-C$_1$–C$_4$-alkyl-silyloxy groups, di-C$_1$–C$_4$-alkylamino groups, di-C$_6$–C$_{10}$-arylamino groups, di-C$_7$–C$_{12}$-aryalkylamino groups, and C$_6$–C$_{10}$—Ar—C$_1$–C$_4$-alkyl groups.

3. A process according to claim 1 wherein

R$^1$ represents hydrogen, C$_1$–C$_4$-alkyl, or fluorine- and/or chlorine-substituted C$_1$–C$_4$-alkyl, R$^2$ and R$^3$ are identical and each represents unsubstituted C$_1$–C$_4$-alkyl, C$_1$–C$_4$-alkoxy, phenyl, or benzyl, R$^4$ represents hydrogen, C$_1$–C$_4$-alkyl or fluorine- and/or chlorine-substituted C$_1$–C$_4$-alkyl, C$_2$–C$_4$-alkenyl or fluorine- and/or chlorine-substituted C$_2$–C$_4$-alkenyl, or phenyl or fluorine-, trifluoromethyl- and/or chlorine-substituted phenyl, $R^5$ represents hydrogen, $C_1$–$C_4$-alkyl or fluorine- and/or chlorine-substituted $C_1$–$C_4$-alkyl, or phenyl or fluorine- and/or chlorine-substituted phenyl, or $R^4$ and $R^5$ together represent a bridge of one of the formulae (II) to (IV) wherein m represents 3 or 4 and n and p or p' independently of one another each represent 1 or 2, $R^6$ represents hydrogen or together with $R^5$ represents —$CH_2$—$CH_2$—, $R^7$ represents unsubstituted $C_1$–$C_4$-alkyl, phenyl, or benzyl, $R^8$ and $R^9$ independently of one another each represent ethyl, i-propyl, n-butyl, or $C_5$–$C_7$-cycloalkyl, and X represents MgBr or $ZnR^8$.

4. A process according to claim 1 wherein (1) from 0.7 to 5 mols of an olefin of the formula (VII) are employed per mole of a carboxamide of the formula (VI), (2) from 0.9 to 1.5 equivalents of an orthometallate of the formula (IX) are employed per equivalent of a carboxamide of the formula (VI), (3) either (a) at least 2.4 mols of a compound of the formula (VIII) when X represents a halogen-containing radical or (b) at least 1.2 mols of a compound of the formula (VIII) when X represents $ZnR^7$ are employed per mole of a carboxamide of the formula (VI).

5. A process according to claim 1 wherein the compound of the formula (VIII) is added at from −40 to +67° C.

6. A process according to claim 1 wherein after addition of the compound of the formula (VIII) has been completed, stirring is continued at from +10 to +70° C. for from 30 minutes to 5 hours.

7. A process according to claim 1 wherein the total reaction time from the beginning of the addition of the compound of the formula (VIII) is from 1 to 24 hours.

* * * * *